United States Patent [19]
Sprecker et al.
[11] 4,321,164
[45] Mar. 23, 1982

[54] 2,4,6-TRIMETHYLCYCLOHEXANEMETHANOL AND DERIVATIVES, PROCESS FOR PREPARING SAME AND ORGANOLEPTIC USES THEREOF

[75] Inventors: Mark A. Sprecker, Sea Bright; Frederick L. Schmitt, Holmdel; Manfred H. Vock, Locust; Joaquin F. Vinals, Red Bank, all of N.J.; Jacob Kiwala, Brooklyn, N.Y.

[73] Assignee: International Flavors & Fragrances Inc., New York, N.Y.

[21] Appl. No.: 195,629

[22] Filed: Oct. 9, 1980

Related U.S. Application Data

[60] Division of Ser. No. 82,076, Oct. 5, 1979, which is a continuation-in-part of Ser. No. 953,128, Oct. 20, 1978, Pat. No. 4,195,099.

[51] Int. Cl.[3] .......................... A61K 7/46; C11B 9/00

[52] U.S. Cl. ................................ 252/522 R; 424/48; 252/174.11; 426/534; 131/276

[58] Field of Search .................................. 252/522 R

[56] References Cited

U.S. PATENT DOCUMENTS 3,956,392 5/1976 deHaan et al. ................ 252/522 R
4,072,719 2/1978 Naegeli .......................... 252/522 R
4,119,576 10/1978 Sprecker et al. .............. 252/522 R

OTHER PUBLICATIONS

Arctander *Perfume and Flavor Chemicals* published by Author, Montclair, N.J. 1969, Monographs 767, 768.

*Primary Examiner*—John F. Niebling
*Attorney, Agent, or Firm*—Arthur L. Liberman

[57] ABSTRACT

Described are 2,4,6-Trimethylcyclohexanemethanol derivatives having the generic structure:

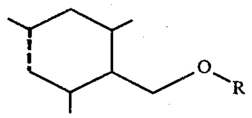

wherein the dashed line represents a carbon-carbon single bond or a carbon-carbon double bond and R is hydrogen or acetyl. The 2,4,6-Trimethylcyclohexanemethanol and derivatives thereof are useful in perfumery and foodstuff, medicinal product and smoking tobacco flavors.

1 Claim, 12 Drawing Figures

GLC PROFILE FOR EXAMPLE II.

GLC PROFILE FOR EXAMPLE I.

I R SPECTRUM FOR EXAMPLE I.

GLC PROFILE FOR EXAMPLE IV.

GLC PROFILE FOR EXAMPLE III.

2,4,6-TRIMETHYLCYCLOHEXANEMETHANOL AND DERIVATIVES, PROCESS FOR PREPARING SAME AND ORGANOLEPTIC USES THEREOF

This is a divisional of application Ser. No. 082,076, filed Oct. 5, 1979, which is a continuation-in-part of Ser. No. 953,128 filed on Oct. 20, 1978, now U.S. Pat. No. 4,195,099 issued Mar. 25, 1980.

BACKGROUND OF THE INVENTION

The instant invention provides novel 2,4,6-Trimethylcyclohexanemethanol and derivatives thereof having the generic structure:

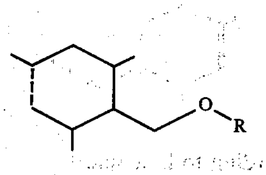

wherein R is hydrogen or acetyl and wherein the dashed line is a carbon-carbon single bond or a carbon-carbon double bond and uses thereof for their organoleptic properties in consumable materials.

Chemical compounds which can provide sweet, spicy; fresh, green, floral; fruity; Fressia-like and methyl ionone-like aromas with geranium and ionone-like topnotes and minty-rose undertones are desirable in the art of perfumery. Many of the natural materials which provide such fragrances and contribute such desired nuances to perfumery compositions are high in cost, unobtainable at times, vary in quality from one batch to another and/or are generally subject to the usual variations of natural products.

By the same token, materials which can provide herbaceous, spicy, floral, green, minty, fruity, fresh, ionone-like and camphoraceous flavor characteristics, as well as aroma characteristics, are desirable in applying the art of flavoring to foodstuffs, toothpastes, chewing gums and medicinal products. Many of the natural materials which provide such flavor notes and contribute desired nuances to flavoring compositions are high in cost, vary in quality from one batch to another and/or are generally subject to the usual variations of natural products.

By the same token, sweet, floral, green, weedy and herbaceous aromas prior to and on smoking in the main stream and in the side stream are desirable in the smoking tobacco art for enhancing certain specialty smoking tobacco-like notes.

There is, accordingly, a continuing effort to find synthetic materials which will replace, enhance or augment the essential flavor and fragrance notes provided by natural essential oils or compositions thereof. Unfortunately, many of these synthetic materials either have the desired nuances only to a relatively small degree or else contribute undesirable or unwanted odor to the compositions.

The compound having the structure:

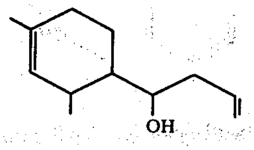

and the compound having the structure:

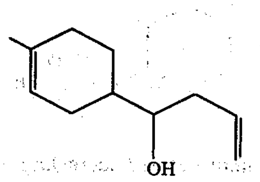

are reported by Sopov and Kovner at Zh. Obsch. Khim. 34, 1492–6 (1964) as abstracted in Chem. Abstracts, Vol. 61, 5529b.

The Sopov and Kovner reference does not, however, disclose organoleptic uses of the compounds having the structures:

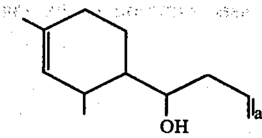
and
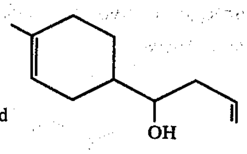

In recent years, compounds having the structures:

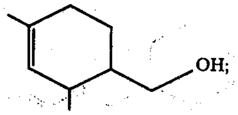

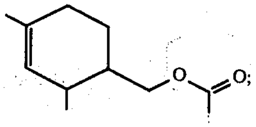

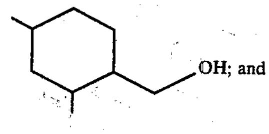
and

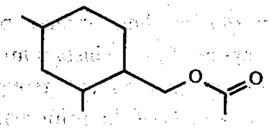

have been found to be useful in compounding various perfume formulations. These lower adjacent methyl homologs of the compounds having the structure:

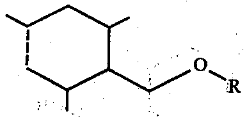

have properties from an organoleptic standpoint considered to be different in kind, rather than in degree, from the compounds defined by the structure:

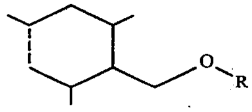

These compounds defined according to the structure:

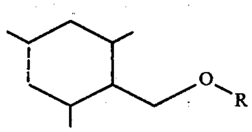

have properties which are unobvious, unexpected and advantageous over the prior-used compounds having the structures:

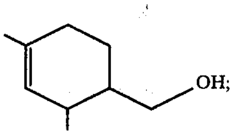

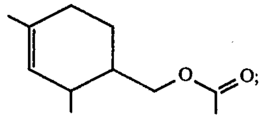

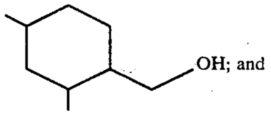

and

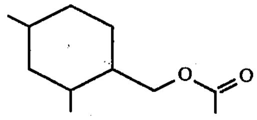

Furthermore, insofar as their organoleptic uses are concerned, the compounds of the instant invention have unexpected, unobvious and advantageous properties over any other compounds of the prior art.

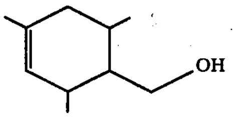

Figure 2:
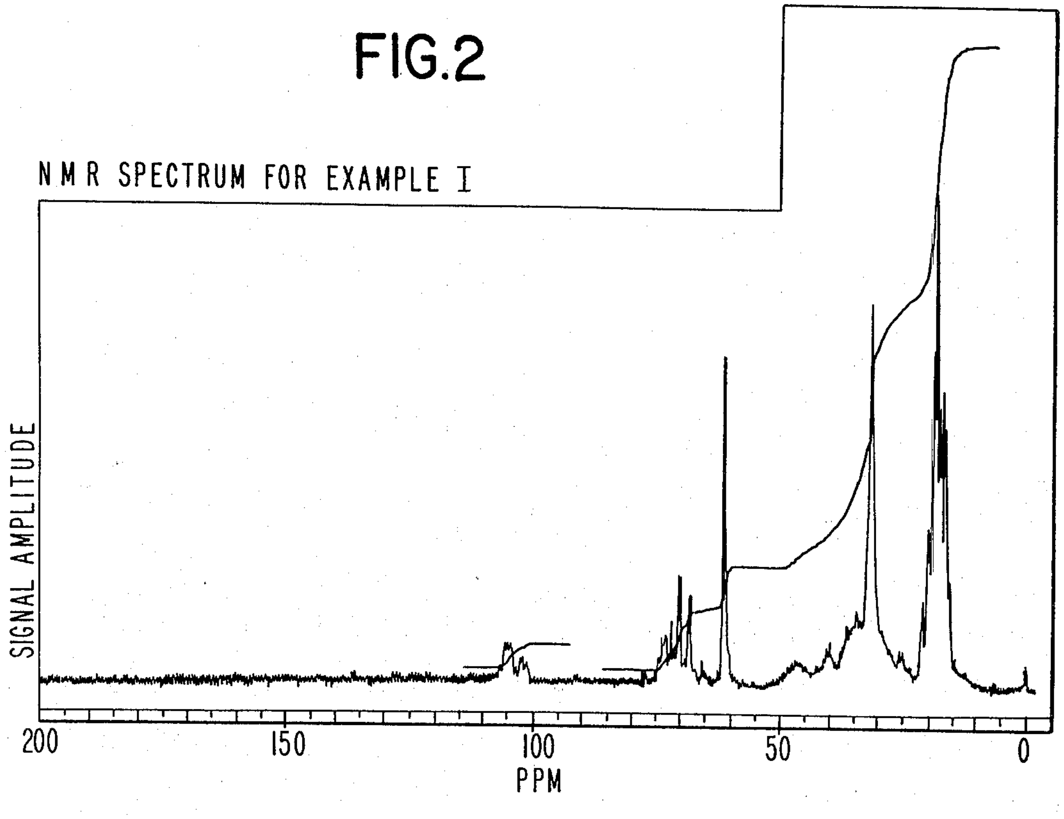

FIG. 2 is the NMR spectrum for the compound having the structure:

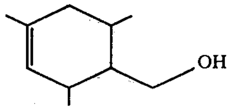

produced according to Example I.

Figure 3:
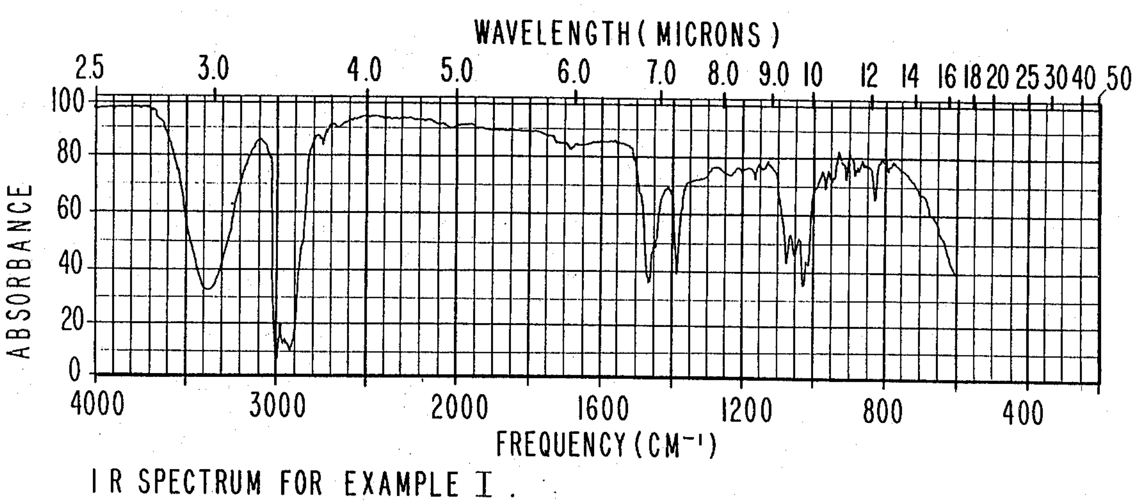

FIG. 3 is the IR spectrum for the compound having the structure:

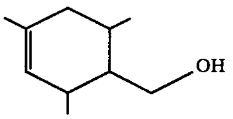

produced according to Example I.

Figure 4:
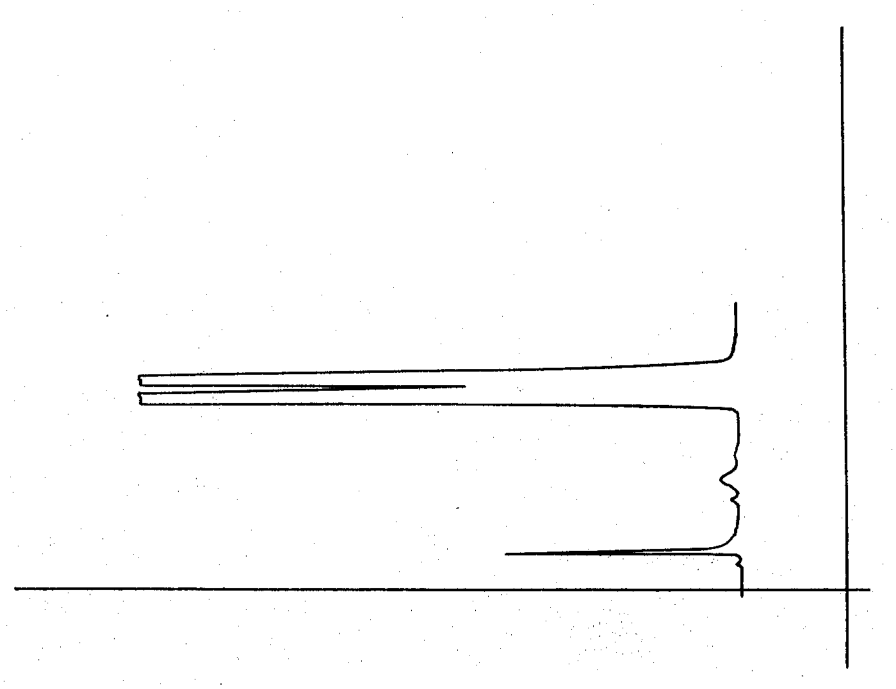

FIG. 4 is the GLC profile for the compound having the structure:

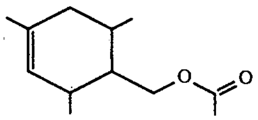

produced according to Example II.

Figure 5:
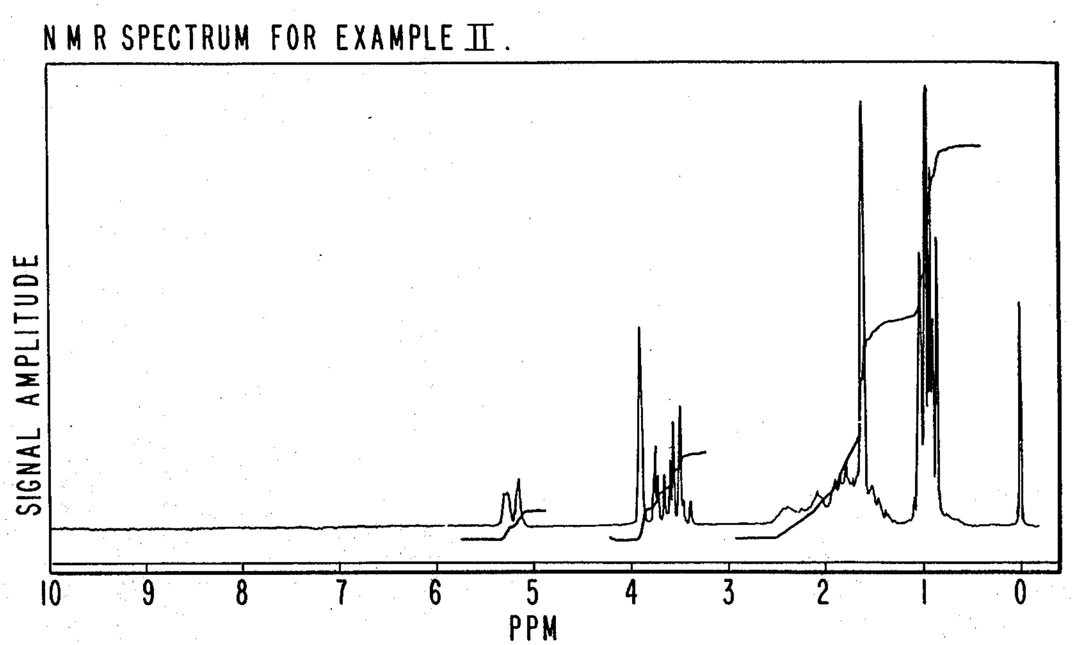

FIG. 5 is the NMR spectrum for the compound having the structure:

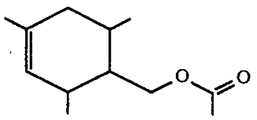

produced according to Example II.

Figure 6:
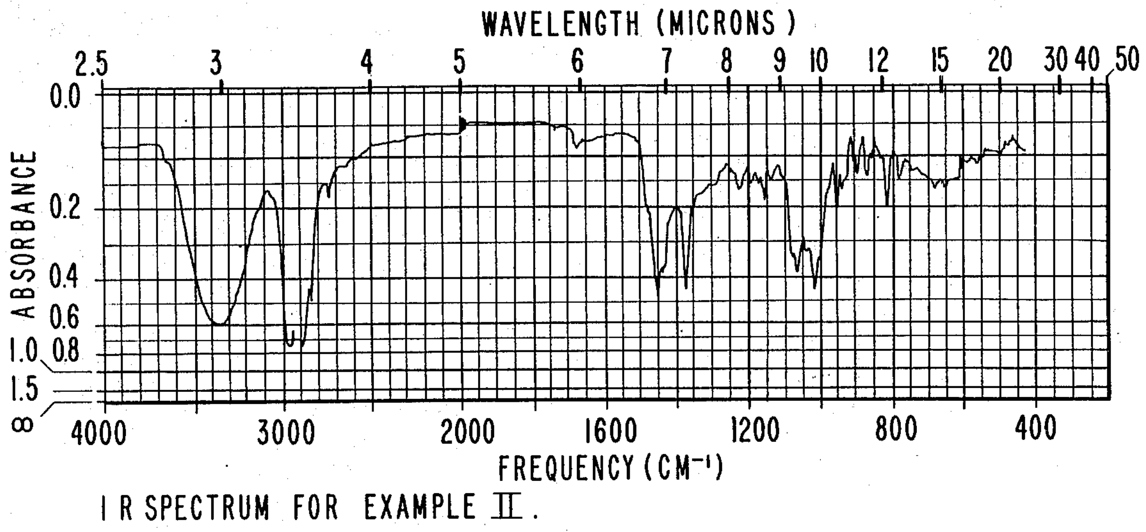

FIG. 6 is the infra-red spectrum for the compound having the structure:

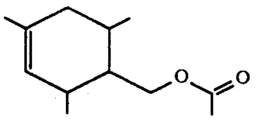

produced according to Example II.

Figure 7:
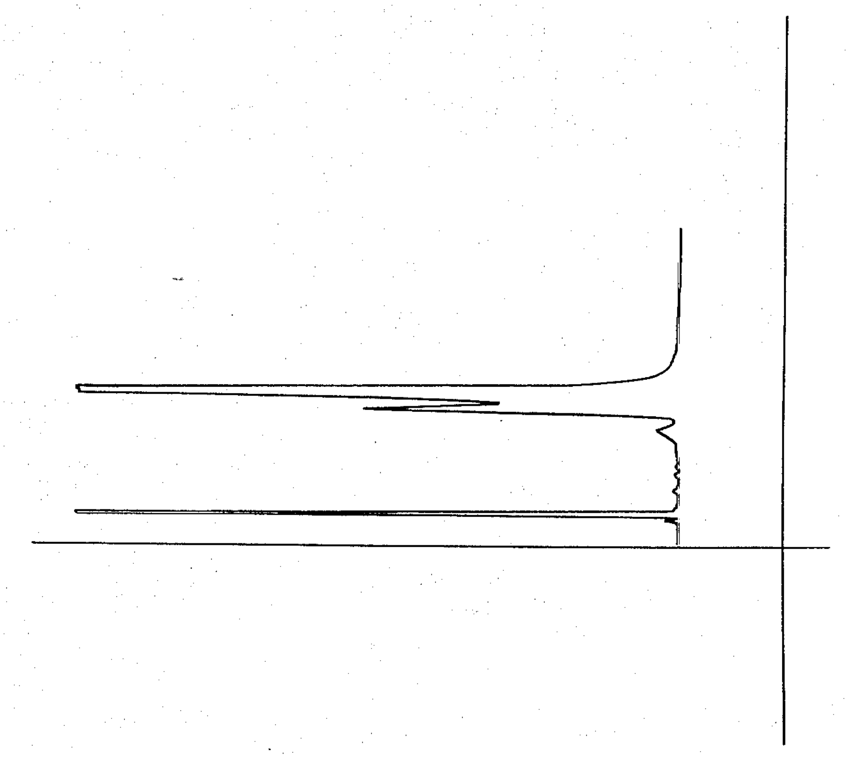

FIG. 7 is the GLC profile for the reaction product of Example III containing the compound having the structure:

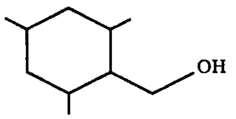

Figure 8:
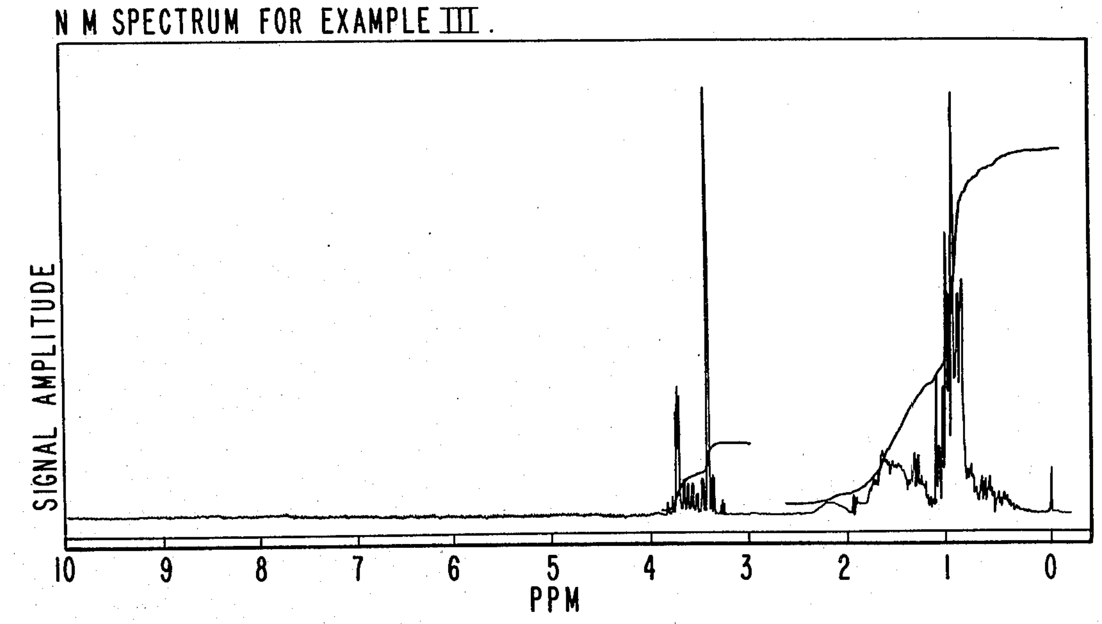

FIG. 8 is the NMR spectrum for the compound having the structure:

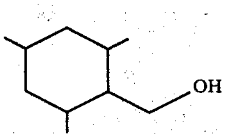

produced according to Example III.

Figure 9:
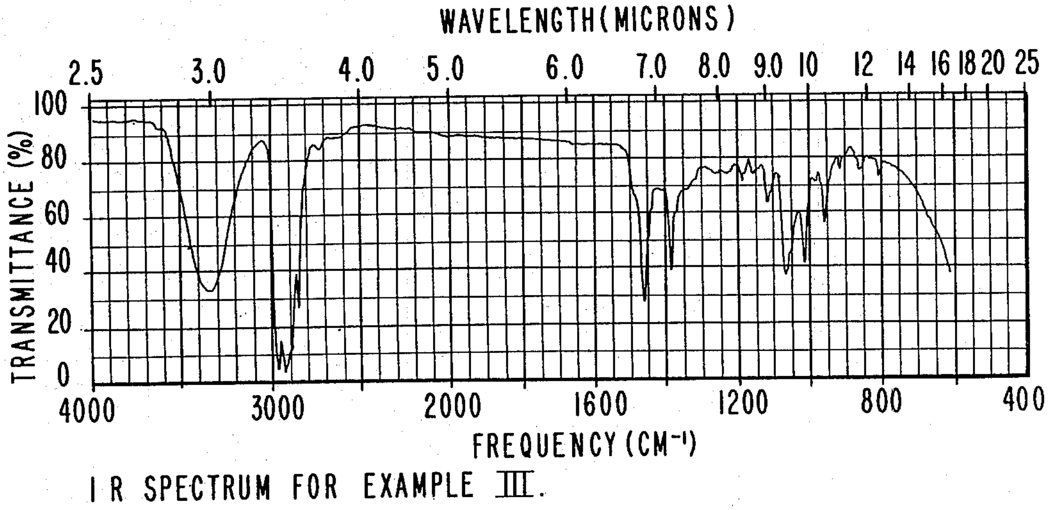

FIG. 9 is the infra-red spectrum for the compound having the structure:

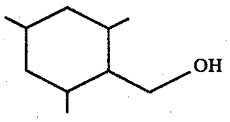

produced according to Example III.

Figure 10:
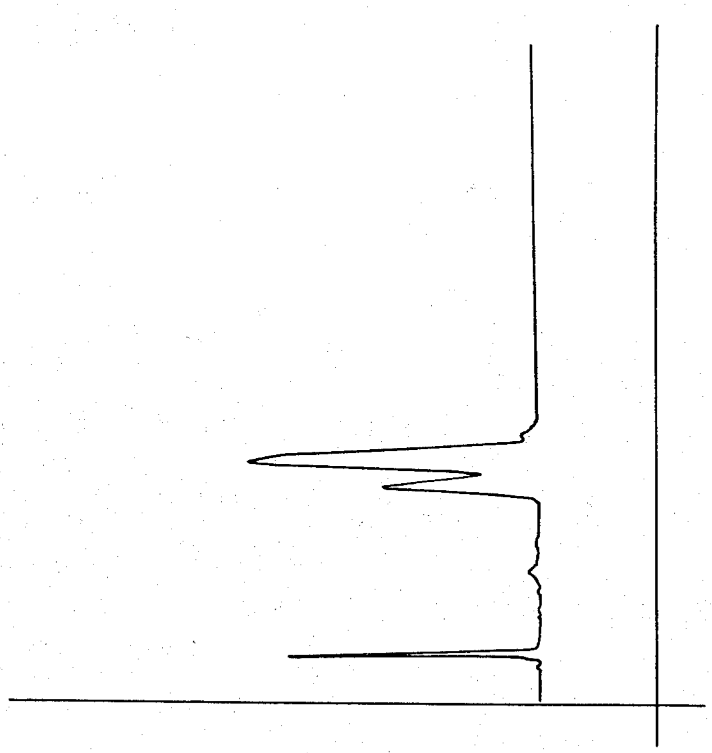

FIG. 10 is the GLC profile for the reaction product of Example IV having the structure:

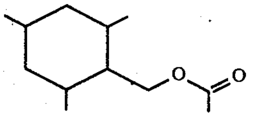

Figure 11:
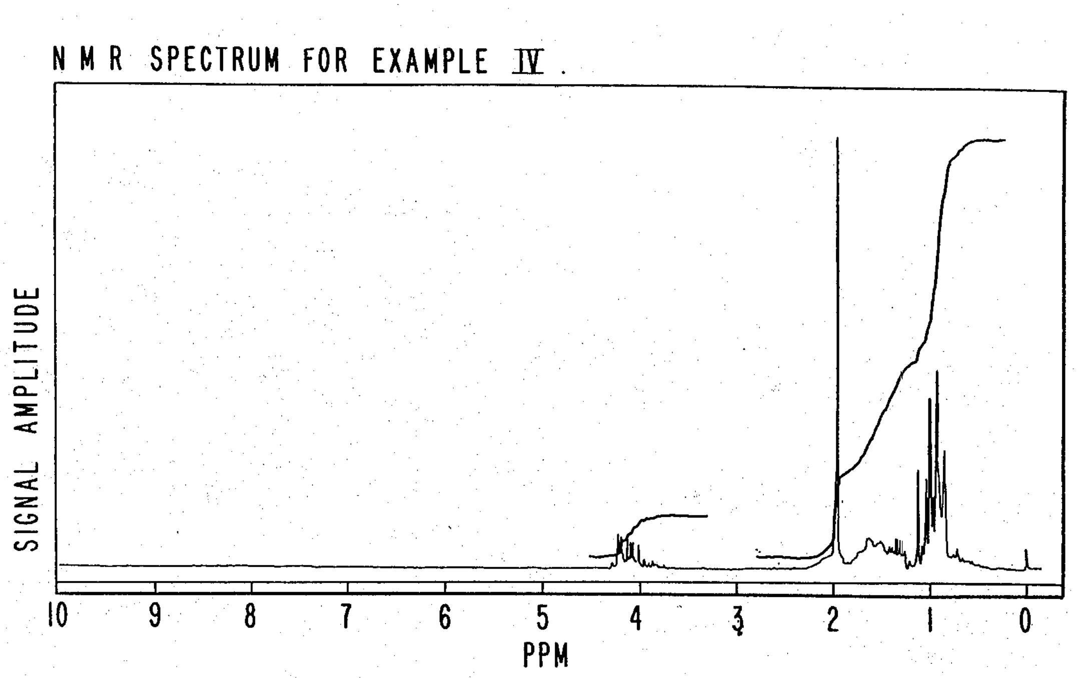

FIG. 11 is the NMR spectrum for the compound having the structure:

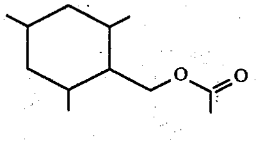

produced according to Example IV.

Figure 12:
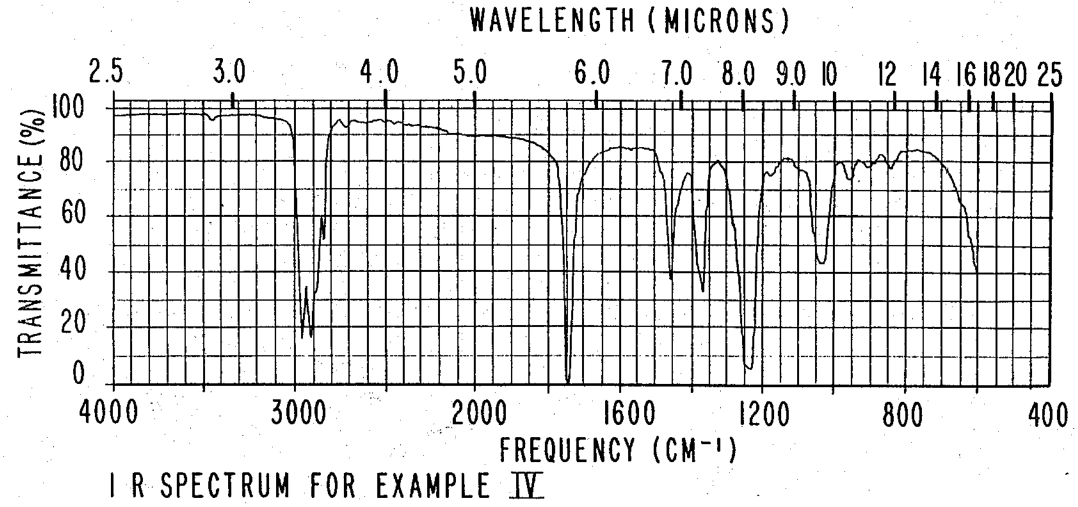

FIG. 12 is the infra-red spectrum for the compound having the structure:

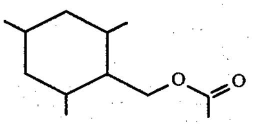

produced according to Example IV.

THE INVENTION

It has now been determined that certain 2,4,6-Trimethylcyclohexanemethanol derivatives and the 2,4,6-Trimethylcyclohexanemethanol itself having the generic structure:

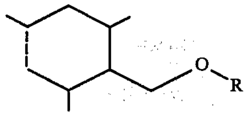

wherein the dashed line represents a carbon-carbon signal bond or a carbon-carbon double bond and R is hydrogen or acetyl are capable of imparting a variety of flavors and fragrances to various consumable materials and are also capable of augmenting or enhancing a variety of flavors and fragrances of various consumable materials.

Briefly, our invention contemplates augmenting or enhancing the flavors and/or fragrances of such consumable materials as perfumes, perfumed articles (e.g., solid or liquid anionic, cationic or non-ionic detergents or dryer-added fabric softeners), colognes, foodstuffs, chewing gums, toothpastes, medicinal products and smoking tobaccos by adding thereto a small but effective amount of at least one of the compounds having the generic structure:

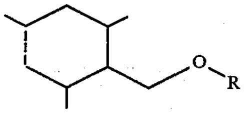

wherein the dashed line represents a carbon-carbon single bond or a carbon-carbon double bond and R is hydrogen or acetyl.

The 2,4,6-Trimethylcyclohexanemethanol and derivatives thereof of our invention augment or enhance camphoraceous, herbaceous, spicy, floral, green, minty, fruity, fresh and ionone-like flavor and aroma characteristics insofar as augmenting or enhancing the aroma or taste of foodstuffs, toothpastes, medicinal products (e.g., cough drops) and chewing gum.

The 2,4,6-Trimethylcyclohexanemethanol and derivatives thereof of our invention also augment or enhance the sweet, spicy; fresh, green, floral, fruity; Freesia; methyl ionone-like aromas and geranium and ionone topnotes and minty-rose undertones of perfumes, perfumed articles (such as cationic, anionic and non-ionic detergents and dryer-added fabric softener articles) and colognes.

The 2,4,6-Trimethylcyclohexanemethanol and derivatives of our invention also augment or enhance the sweet, floral, green, weedy and herbaceous aroma nuances of smoking tobacco, both prior to and on smoking, both in the main stream and in the side stream.

Examples of the 2,4,6-Trimethylcyclohexanemethanol and derivatives of our invention and their organoleptic characteristics are as follows:

TABLE I

| STRUCTURE OF COMPOUND | NAME OF COMPOUND | FOODSTUFF FLAVOR CHARACTERISTICS | FRAGRANCE CHARACTERISTICS | SMOKING TOBACCO FLAVOR CHARACTERISTICS |
|---|---|---|---|---|
| 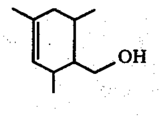 | 2,4,6-Trimethyl-3-cyclohexene-1-methanol | A camphoraceous, herbaceous and spicy aroma with camphoraceous and bitter flavor characteristics at 5 ppm. | A fresh, green, floral (flower shop note) with some geranium character. | A sweet, floral and green aroma prior to and on smoking in the main stream and the side stream. |

TABLE I-continued

| STRUCTURE OF COMPOUND | NAME OF COMPOUND | FOODSTUFF FLAVOR CHARACTERISTICS | FRAGRANCE CHARAC-TERISTICS | SMOKING TOBACCO FLAVOR CHARAC-TERISTICS |
|---|---|---|---|---|
| 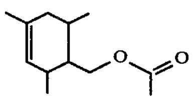 | 2,4,6-Trimethyl-3-cyclohexene-1-methan-olacetate | A floral, green, herb-aceous and minty aroma character and a minty, herbaceous and green flavor characteristic at 10 ppm. | A fresh, fruity floral (Freesia-like) aroma with ionone-like nuan-ces. | A sweet, floral, green weedy and herbaceous aroma characteristic prior to and on smoking in the main stream and the side stream. |
| 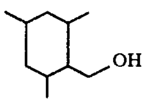 | 2,4,6-Trimethylcyclo-hexanemethanol | A minty, herbaceous, fruity, floral and fresh aroma characteristic with sweet, minty, and herbaceous flavor characteristics at 2 ppm making it useful in the mint, spearmint and "oral hygiene" type flavors. | A sweet, spicy, green, floral-like aroma with a minty-rose background. | |
| 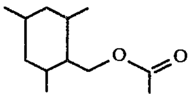 | 2,4,6-Trimethylcyclo-hexanemethanolacetate | Minty, herbaceous, fruity, floral, ionone-like oriental and fresh aroma nuances with herbaceous and floral flavor characteristics at 2 ppm making it use-ful in the "oral hygiene" area. | A methylionone-like, spicy, fruity aroma. | |

The 2,4,6-Trimethylcyclohexanemethanol and derivatives thereof of our invention can be produced by first forming 2,4,6-Trimethyl-3-cyclohexene-1-carboxaldehyde by reaction of an alpha, beta-unsaturated aldehyde with a conjugated diene according to the reaction:

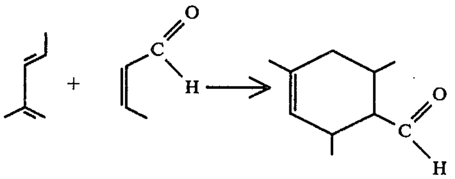

This reaction product is then reduced using an alkali metal borohydride or hydrogen and a Raney nickel catalyst. Also lithium aluminum hydride and an alkali metal $BH_3CN$ can be used.

The mole ratio of the resulting isocyclocitral to alkali metal borohydride may vary from 5:1 to 2:1 but is preferably 4:1. The reaction temperature for reduction may range from 40° C. up to 80° C. The solvents used in this reduction reaction are polar solvents such as tetrahydrofuran, isopropyl alcohol, methyl alcohol, ethyl alcohol and dioxane.

The procedure for carrying out the reaction is critical insofar as one particular aspect is concerned; that is, that the isocyclocitral is to be added to a mixture of alkali metal borohydride in solvent.

Regarding the catalytic hydrogenation of the 2,4,6-Trimethyl-3-cyclohexene-1-carboxaldehyde, Raney nickel is the preferred catalyst. The temperature of reaction may vary from 60° C. up to 100° C. with a temperature of 80° C. being preferred. The hydrogen pressure when using hydrogen over a Raney nickel catalyst may vary up to 500 psig.

The 2,4,6-Trimethyl-3-cyclohexene-1-methanol prepared by the reduction of the 2,4,6-Trimethyl-3-cyclohexene-1-carboxaldehyde may be either further reduced to form the compound having the structure:

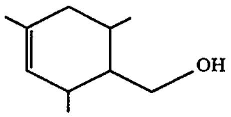

or it may be acylated using, for example, acetic anhydride to form the compound having the structure:

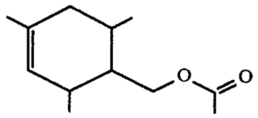

In addition, the compound having the structure:

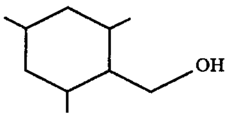

may also be acylated thereby producing the compound having the structure:

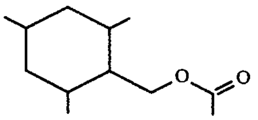

Although the preferred reagent for such acylation is acetic anhydride, acetyl chloride in a base such as pyridine, triethylamine or potassium carbonate may be used.

When using acetic anhydride as an acylating agent, this reaction can be carried out in the presence of mineral acids such as phosphoric acid, sulfuric acid or anhydrous hydrochloric acid at temperatures of from 40° C. up to 80° C. When no catalyst is used, the temperature range should be from 80° C. up to 120° C. Inert solvents in this reaction can be used, such as toluene, dichlorobenzene or xylene, or the reaction can be carried out without the use of a solvent.

The mole ratio of an acylating agent:starting material is 1:1 up to 2:1 with a mole ratio of 1.5:1 being preferred.

In carrying out the hydrogenation using Raney nickel, 5% or 10% palladium or platinum on carbon can be used to replace the Raney nickel or rhodium catalyst may be used. Raney nickel is preferred as the catalyst since it is the least expensive to use and since the temperatures when using same are relatively low. The reaction pressure may vary during the hydrogenation from 500 psi up to 3,600 psi with 1,000 psi pressure being preferred. The overall reaction sequence as described above is set forth as follows:

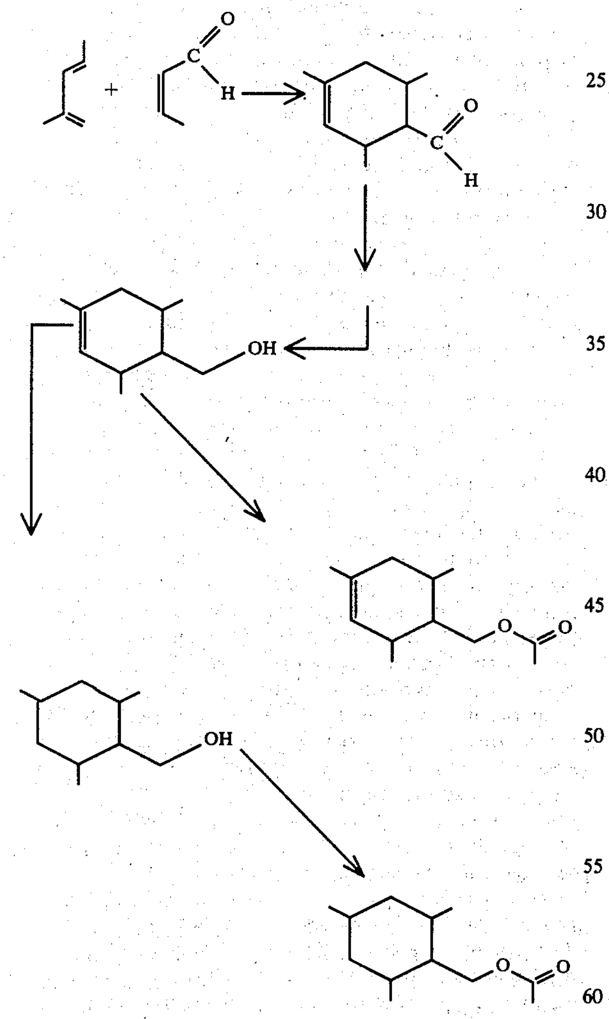

The individual 2,4,6-Trimethylcyclohexanemethanol and derivatives thereof of our invention can be obtained in pure form or in substantially pure form by conventional purification techniques. Thus, the products can be purified and/or isolated by distillation, extraction, crystallization, preparative chromatographic techniques (column chromatography and vapor phase chromatography) and the like. It has been found desirable to purify the 2,4,6-Trimethylcyclohexanemethanol and derivatives thereof of our invention by fractional distillation in vacuo.

When the 2,4,6-Trimethylcyclohexanemethanol and derivatives thereof our invention are used as food flavor adjuvants, the nature of the co-ingredients included with said 2,4,6-Trimethylcyclohexanemethanol and derivatives thereof of our invention in formulating the product composition will also serve to alter modify, augment or enhance the organoleptic characteristics of the ultimate foodstuff treated therewith.

As used herein in regard to flavors, the terms "alter", "modify" and "augment" in their various forms means "supplying or imparting flavor character or note to otherwise bland, relatively tasteless substances or augmenting the existing flavor characteristic where a natural flavor is deficient in some regard or supplementing the existing flavor impression to modify its quality, character or taste".

The term "enhance" is used herein to mean the intensification of a flavor or aroma characteristic or note without the modification of the quality thereof. Thus, "enhancement" of a flavor or aroma means that the enhancement agent does not add any additional flavor note.

As used herein, the term "foodstuff" includes both solid and liquid ingestible materials which usually do, but need not, have nutritional value. Thus, foodstuffs include soups, convenience foods, beverages, dairy products, candies, vegetables, cereals, soft drinks, snacks, and the like.

As used herein, the term "medicinal product" includes both solids and liquids which are ingestible, nontoxic materials which have medicinal value such as cough syrups, cough drops, aspirin and chewable medicinal tablets.

The term "chewing gum" is intended to mean a composition which comprises a substantially water insoluble, chewable plastic gum base such as chicle, or substitutes therefor, including jelutong, guttakay, rubber or certain comestible natural or synthetic resins or waxes. Incorporated with the gum base in admixture therewith may be plasticizers or softening agents, e.g., glycerine, and a flavoring composition which incorporates one or more of 2,4,6-Trimethylcyclohexanemethanol and derivatives thereof of our invention, and in addition, sweetening agents which may be sugars, including sucrose or dextrose and/or artificial sweeteners such as cyclamates or saccharin. Other optional ingredients may also be present.

Substances suitable for use herein as co-ingredients or flavoring adjuvants are well known in the art for such use, being extensively described in the relevant literature. It is a requirement that any such material be "ingestibly" acceptable and thus non-toxic and otherwise non-deleterious particularly from an organoleptic standpoint whereby the ultimate flavor and/or aroma of the consumable material used is not caused to have unacceptable aroma and taste nuances. Such materials may in general be characterised as flavoring adjuvants or vehicles comprising, broadly, stabilizers, thickeners, surface active agents, conditioners, other flavorants and flavor intensifiers.

Stabilizer compounds include preservatives, e.g., sodium chloride; antioxidants, e.g., calcium and sodium ascorbate, ascorbic acid, butylated hydroxyanisole (mixture of 2- and 3-tertiary-butyl-4-hydroxy anisole), butylated hydroxytoluene (2,6-di-tertiary-butyl-4-methyl phenol), propyl gallate and the like, and sequestrants, e.g., citric acid.

Thickener compounds include carriers, binders, protective colloids, suspending agents, emulsifiers and the like, e.g., agar agar, carrageenan; cellulose and cellulose derivatives such as carboxymethyl cellulose and methyl cellulose; natural and synthetic gums such as gum arabic, gum tragacanth; gelatin, proteinaceous materials; lipids, carbohydrates; starches, pectins, and emulsifiers, e.g., mono- and diglycerides of fatty acids, skim milk powder, hexoses, pentoses, disaccharides, e.g., sucrose, corn syrup and the like.

Surface active agents include emulsifying agents, e.g., fatty acids such as capric acid, caprylic acid, palmitic acid, myristic acid and the like, mono- and diglycerides of fatty acids, lecithin, defoaming and flavor-dispersing agents such as sorbitan monostearate, potassium stearate, hydrogenated tallow alcohol and the like.

Conditioners include compounds such as bleaching and maturing agents, e.g., benzoyl peroxide, calcium peroxide, hydrogen peroxide and the like; starch modifiers such as peracetic acid, sodium chlorite, sodium hypochlorite, propylene oxide, succinic anhydride and the like, buffers and neutralizing agents, e.g., sodium acetate, ammonium bicarbonate, ammonium phosphate, citric acid, lactic acid, vinegar and the like; colorants, e.g., carminic acid, cochineal, tumeric and curcuma and the like, firming agents such as aluminum sodium sulfate, calcium chloride and calcium gluconate; texturizers, anti-caking agents, e.g., aluminum calcium sulfate and tribasic calcium phosphate; enzymes; yeast foods, e.g., calcium lactate and calcium sulfate; nutrient supplements, e.g., iron salts such as ferric phosphate, ferrous gluconate and the like, riboflavin, vitamins, zinc sources such as zinc chloride, zinc sulfate and the like.

Other flavorants and flavor intensifiers include organic acids, e.g., acetic acid, formic acid, 2-hexenoic acid, benzoic acid, n-butyric acid, caproic acid, caprylic acid, cinnamic acid, isobutyric acid, isovaleric acid, alpha-methylbutyric acid, propionic acid, valeric acid, 2-methyl-2-pentenoic acid, and 2-methyl-3-pentenoic acid; ketones and aldehydes, e.g., acetaldehyde, acetophenone, acetone, acetyl methyl carbinol, acrolein, n-butanal, crotonal, diacetyl, 2-methylbutanal, beta,-beta-dimethyl acrolein, methyl n-amyl ketone, n-hexanal, 2-hexanal, isopentanal, hydrocinnamic aldehyde, cis-3-hexenal, 2-heptenal, nonyl aldehyde, 4-(p-hydroxyphenyl)-2-butanone, alpha-ionone, beta-ionone, 2-methyl-3-butanone, benzaldehyde, beta-damascone, alpha-damascone, beta-damascenone, acetophenone, 2-heptanone, o-hydroxy-acetophenone, 2-methyl-2-hepten-6-one, 2-octanone, 2-undecanone, 3-phenyl-4-pentenal, 2-phenyl-2-hexenal, 2-phenyl-2-pentenal, furfural, 5-methylfurfural, cinnamaldehyde, beta-cyclohomocitral, 2-pentanone, 2-pentenal and propanal; alcohols such as 1-butanol, benzyl alcohol, 1-borneol, trans-2-buten-1-ol, ethanol, geraniol, 1-hexanol, 2-heptanol, trans-2-hexenol-1, cis-3-hexen-1-ol, 3-methyl-3-buten-1-ol, 1-pentanol, 1-penten-3-ol, p-hydroxyphenyl-2-ethanol, isoamyl alcohol, isofenchyl alcohol, phenyl-2-ethanol, alpha-terpineol, cis-terpinhydrate, eugenol, linalool, 2-heptanol, acetoin; esters, such as butyl acetate, ethyl acetate, ethyl acetoacetate, ethyl benzoate, ethyl butyrate, ethyl caprate, ethyl caproate, ethyl carpylate, ethyl cinnamate, ethyl crotonate, ethyl formate, ethyl isobutyrate, ethyl isovalerate, ethyl laurate, ethyl myristate, ethyl alpha-methylbutyrate, ethyl propionate, ethyl salicylate, trans-2-hexenyl acetate, hexyl acetate, 2-hexenyl butyrate, hexyl butyrate, isoamyl acetate, isopropyl butyrate, methyl acetate, methyl butyrate, methyl caproate, methyl isobutyrate, alpha-methylphenylglycidate, ethyl succinate, isobutyl cinnamate, cinnamyl formate, methyl cinnamate, and terpenyl acetate; hydrocarbons such as dimethyl naphthalene, dodecane, methyldiphenyl, methyl naphthalene, myrcene, naphthalene, octadecane, tetradecane, tetramethylnaphthalene, tridecane, trimethylnaphthalene, undecane, caryophyllene, alpha-phellandrene, beta-phellandrene, p-cymene 1-alpha-pinene, beta-pinene, dihydrocarveol; pyrazines such as 2,3-dimethylpyrazine, 2,5-dimethylpyrazine, 2,6-dimethylpyrazine, 3-ethyl-2,5-dimethylpyrazine, 2-ethyl-3,5,6-trimethylpyrazine, 3-isoamyl-2,5-dimethylpyrazine, 5-isoamyl-2,3-dimethylpyrazine, 2-isoamyl-3,5,6-trimethylpyrazine, isopropyl dimethylpyrazine, methyl ethylpyrazine, tetramethylpyrazine, trimethylpyrazine; essential oils such as jasmine absolute, cassia oil, cinnamon bark oil, black pepper oleoresin, oil of black pepper, rose absolute, orris absolute, oil of cubeb, oil of coriander, oil of pimento leaf, oil of patchouli, oil of nutmeg, lemon essential oil, safran oil, Bulgarian rose, capsicum, yara yara and vanilla; lactones such as γ-nonalactone; sulfides, e.g., methyl sulfide and other materials such as maltol, and acetals (e.g., 1,1-diethoxyethane, 1,1-dimethyloxyethane and dimethoxymethane), piperine, chavicine, and piperidine.

The specific flavoring adjuvant selected for use may be either solid or liquid depending upon the desired physical form of the ultimate product, i.e., foodstuff, whether simulated or natural, and should, in any event, (i) be organoleptically compatible with 2,4,6-Trimethylcyclohexanemethanol and derivatives thereof of our invention by not covering or spoiling the organoleptic properties (aroma and/or taste) thereof; (ii) be non-reactive with 2,4,6-Trimethylcyclohexanemethanol and derivatives thereof of our invention and (iii) be capable of providing an environment in which the 2,4,6-Trimethylcyclohexanemethanol and derivatives thereof of our invention can be dispersed or admixed to provide a homogeneous medium. In addition, selection of one or more flavoring adjuvants, as well as the quantities thereof will depend upon the precise organoleptic character desired in the finished product. Thus, in the case of flavoring compositions, ingredient selection will vary in accordance with the foodstuff, chewing gum, medicinal product or toothpaste to which the flavor and/or aroma are to be imparted, modified, altered or enhanced. In contradistinction, in the preparation of solid products, e.g., simulated foodstuffs, ingredients capable of providing normally solid compositions should be selected such as various cellulose derivatives.

As will be appreciated by those skilled in the art, the amount of 2,4,6-Trimethylcyclohexanemethanol and derivatives thereof of our invention employed in a particular instance can vary over a relatively wide range, depending upon the desired organoleptic effects to be achieved. Thus, correspondingly, greater amounts would be necessary in those instances wherein the ultimate food composition to be flavored (e.g., with a spice flavor or a specific black pepper-like flavor) is relatively bland to the taste, whereas relatively minor quantities may suffice for purposes of enhancing the composition merely deficient in natural flavor or aroma. The primary requirement is that the amount selected be effective, i.e., sufficient to alter, modify or enhance the organoleptic characteristics of the parent composition, whether foodstuff per se, chewing gum per se, medicinal product per se, toothpaste per se, or flavoring composition.

The use of insufficient quantities of 2,4,6-Trimethylcyclohexanemethanol and derivatives thereof of our invention will, of course, substantially vitiate any possibility of obtaining the desired results while excess quantities prove needlessly costly and in extreme cases may disrupt the flavor-aroma balance, thus proving self-defeating. Accordingly, the terminology "effective amount" and "sufficient amount" is to be accorded a significance in the context of the present invention consistent with the obtention of desired flavoring effects.

Thus, and with respect to ultimate food compositions, chewing gum compositions, medicinal product compositions and toothpaste compositions, it is found that quantities of 2,4,6-Trimethylcyclohexanemethanol and derivatives thereof of our invention ranging from a small but effective amount, e.g., 0.05 parts per million up to about 500 parts per million based on total composition, are suitable. Concentrations in excess of the maximum quantity stated are not normally recommended since they fail to provide commensurate enhancement of organoleptic properties. In those instances wherein the 2,4,6-Trimethylcyclohexanemethanol and derivatives thereof of our invention are added to the foodstuff as an integral component of a flavoring composition, it is, of course, essential that the total quantity of flavoring composition employed be sufficient to yield effective 2,4,6-Trimethylcyclohexanemethanol and derivatives thereof concentration in the foodstuff product.

Food flavoring compositions prepared in accordance with the present invention preferably contain the 2,4,6-Trimethylcyclohexanemethanol and derivatives thereof of our invention in concentrations ranging from about 0.025% up to about 15% by weight based on the total weight of the said flavoring composition.

The composition described herein can be prepared according to conventional techniques well known as typified by cake batters and fruit drinks and can be formulated by merely admixing the involved ingredients within the proportions stated in a suitable blender to obtain the desired consistency, homogeneity of dispersion, etc. Alternatively, flavoring compositions in the form of particulate solids can be conveniently prepared by mixing the 2,4,6-Trimethylcyclohexanemethanol and derivatives thereof of our invention with, for example, gum arabic, gum tragacanth, carrageenan and the like, and thereafter spray-drying the resultant mixture whereby to obtain the particular solid product. Pre-prepared flavor mixes in powder form, e.g., a fruit-flavored powder mix, are obtained by mixing the dried solid components, e.g., starch, sugar and the like, and 2,4,6-Trimethylcyclohexanemethanol and derivatives thereof of our invention in a dry blender until the requisite degree of uniformity is achieved.

It is presently preferred to combine with the 2,4,6-Trimethylcyclohexanemethanol and derivatives thereof of our invention, the following adjuvants: Oil of Cubeb; Phellandrene; beta-Phellandrene; Oil of Coriander; Oil of Pimento Leaf, Oil of Patchouli; Natural Lemon Oil; Acetaldehyde; α-Terpineol; Citral; Carvone; Terpinolene; α-Terpinene; Diphenyl; α-Fenchyl Alcohol; Cineole; Limonene; Linalool; Geranyl Acetate; Nootkatone; Neryl Acetate; Heliotropin; Maltol, Vanillin; Ethyl Maltol; Ethyl Vanillin; Anisaldehyde; Alpha Pinene; Beta-Pinene; Beta-Caryophyllene; Dihydrocarveol; Piperonal; Piperine; Chavicine; Piperidine; Oil of Black Pepper; Black Pepper Oleoresin; Capsicum; Oil of Nutmeg; Cardamom Oil; Clove Oil; Separmint Oil; Oil of Peppermint; and $C_{10}$-Terpinyl Ethers as described in application for U.S. Letters Patent, Ser. No. 872,937 filed on Jan. 27, 1978, now U.S. Pat. No. 4,131,687 issued on Dec. 26, 1978 (such as fenchyl ethyl ethers).

The 2,4,6-Trimethylcyclohexanemethanol and derivatives thereof of our invention can be used to contribute sweet, spicy, fresh green, floral, fruity, Freesia-like and methylionone-like aromas with geranium and ionone-like topnotes and minty-rose undertones to perfumes, perfumed articles and colognes. As olfactory agents, the 2,4,6-Trimethylcyclohexanemethanol and derivatives thereof of our invention can be formulated into or used as components of a "perfume composition" or can be used as components of a "perfumed article" or the perfume composition may be added to perfumed articles.

The term "perfume composition" is used herein to mean a mixture of organic compounds including, for example, alcohols, aldehydes, ketones, nitriles, ethers, lactones, natural essential oils, synthetic essential oils and frequently hydrocarbons which are admixed so that the combined odors of the individual components produce a pleasant or desired fragrance. Such perfume compositions usually contain: (a) the main note or the "bouquet" or foundation-stone of the composition; (b) modifiers which round-off and accompany the main note; (c) fixatives which include odorous substances which lend a particular note to the perfume throughout all stages of evaporation, and substances which retard evaporation; and (d) top-notes which are usually low-boiling, fresh-smelling materials.

In perfume compositions, the individual component will contribute its particular olfactory characteristics, but the overall effect of the perfume composition will be the sum of the effects of each of the ingredients. Thus, the individual compounds of this invention, or mixtures thereof, can be used to alter the aroma characteristics of a perfume composition, for example, by highlighting or moderating the olfactory reaction contributed by another ingredient in the composition.

The amount of 2,4,6-Trimethylcyclohexanemethanol and derivatives thereof of our invention which will be effective in perfume compositions depends on many factors, including the other ingredients, their amounts and the effects which are desired. It has been found that perfume compositions containing as little as 0.5% of 2,4,6-Trimethylcyclohexanemethanol and derivatives thereof of this invention, or even less, can be used to impart an interesting spicy, fruity, Freesia-like and/or green aroma to soaps, liquid and solid cationic, anionic and nonionic detergents, cosmetics, powders, liquid and solid fabric softeners, optical brightener compositions, and other products. The amount employed can range up to 50% or higher and will depend on considerations of cost, nature of the end product, and the effect desired on the finished product and particular fragrance sought.

The 2,4,6-Trimethylcyclohexanemethanol and derivatives thereof of this invention can be used alone or in a perfume composition as an olfactory component in detergents and soaps, space odorants and deodorants; perfumes; colognes, toilet waters; bath salts; hair preparations such as lacquers, brilliantines, pomades, and shampoos; cosmetic preparations such as creams, deodorants, hand lotions, and sun screens; powders such as talcs, dusting powders, face powder, and the like.

When used as an olfactory component of a perfumed article, as little as 0.01% of one of more of 2,4,6-Trimethylcyclohexanemethanol and derivatives thereof will suffice to impart an interesting spicy, fruity, Freesia-like and/or green aroma. Generally no more than 0.5% is required.

In addition, the perfume composition can contain a vehicle or carrier for 2,4,6-Trimethylcyclohexanemethanol and derivatives thereof alone or with other ingredients. The vehicle can be a liquid such as an alcohol such as ethanol, a glycol such as propylene glycol, or the like. The carrier can be an absorbent solid such as a gum or components for encapsulating the composition such as gelatin which can be used to form a capsule wall surrounding the perfume oil, by means of coacervation.

An additional aspect of our invention provides an organoleptically improved smoking tobacco product and additives therefor including methods of making the same which overcome problems heretofore encountered in the creation or enhancement of specific desired natural tobacco-like notes, particularly hay-like notes. Such notes, both prior to and on smoking, in both the main stream and the side stream, may now be readily controlled and maintained at the desired uniform level regardless of variations in the tobacco components of the blend; or the nature of the filter used in conjunction with the smoking tobacco article.

This invention further provides improved tobacco additives and additives for materials used in the fabrication of tobacco articles (particularly smoking tobacco articles) and methods whereby desirable hay-like notes may be imparted to smoking tobacco products and may be readily varied and controlled to produce the desired uniform flavoring characteristics.

In carrying out this aspect of our invention, we add to smoking tobacco materials or a suitable substitute therefor (e.g., dried lettuce leaves) an aroma and flavor additive containing as an active ingredient, one or more of 2,4,6-Trimethylcyclohexanemethanol and derivatives thereof of our invention.

In addition to 2,4,6-Trimethylcyclohexanemethanol and derivatives thereof of our invention, other flavoring and aroma additives may be added to the smoking tobacco material or substitute therefor either separately or in mixture with one or more of the 2,4,6-Trimethylcyclohexanemethanol and derivatives of our invention:

I. Synthetic Materials
- Beta-methylcinnamaldehyde;
- Eugenol;
- Dipentene;
- Damascenone;
- Maltol;
- Ethyl maltol;
- Delta-undecalactone;
- Delta-decalactone;
- Benzaldehyde;
- Amyl acetate;
- Ethyl butyrate;
- Ethyl valerate;
- Ethyl acetate;
- 2-Hexen-1-ol;
- 2-Methyl-5-isopropyl-1,3-nonadiene-8-one;
- 2-Methyl-5-isopropylacetophenone;
- 2-Hydroxy-2,5,5,8α-tetramethyl-1-)2-hydroxyethyl)-decahydronaphthalene;
- Dodecahydro-3α,6,6,9α-tetramethylnaphtho-(2,1-β)-furan;
- 4-Hydroxyhexenoic acid, gamma-lactone;
- Polyisoprenoid hydrocarbons defined in Example V of U.S. Pat. No. 3,589,372 issued on June 29, 1971

II. Natural Oils
- Celery seed oil;
- Coffee extract;
- Bergamot oil;
- Cocoa extract;
- Nutmeg oil;
- Origanum oil.

An aroma and flavoring concentrate containing one or more of 2,4,6-Trimethylcyclohexanemethanol and derivatives thereof of our invention and, if desired, one or more of the above-indicated additional flavoring additives may be added to the smoking tobacco material, to the filter or to the leaf or paper wrapper or to a filter which is part of the smoking article. The smoking tobacco material may be shredded, cured, cased and blended tobacco material or reconstituted tobacco material or tobacco substitutes (e.g., lettuce leaves) or mixtures thereof. The proportions of flavoring additives may be varied in accordance with taste, but insofar as enhancement or the imparting of hay-like notes prior to and on smoking, in both the main stream and the side stream, we have found that satisfactory results are obtained if the proportion by weight of the sum total of 2,4,6-Trimethylcyclohexanemethanol and derivatives thereof of this invention to smoking tobacco material is between 50 ppm and 1500 ppm (0.005%–0.15%) of the active ingredients to the smoking tobacco material. We have further found that satisfactory results are obtained if the proportions by weight of the sum total of 2,4,6-Trimethylcyclohexanemethanol and derivatives thereof used to flavoring material is between 0.05:1 and 0.50:1.

Any convenient method for incorporating the 2,4,6-Trimethylcyclohexanemethanol and derivatives thereof of our invention in the tobacco product may be employed. Thus the 2,4,6-Trimethylcyclohexanemethanol and derivatives thereof of our invention taken alone or along with other flavoring additives may be dissolved in a suitable solvent such as food grade ethanol, pentane, diethyl ether and/or other volatile organic solvents, and the resulting solution may either be sprayed on the cured, cased and blended tobacco material; or the tobacco material or filter may be dipped into such solution. Under certain circumstances, a solution of one or more 2,4,6-Trimethylcyclohexanemethanol and derivatives thereof taken alone or taken further together with other flavoring additives as set forth above, may be applied by means of a suitable applicator such as a brush or roller on the paper or leaf wrapper for the smoking product, or it may be applied to the filter by either spraying or dipping or coating.

Furthermore, it will be apparent that only a portion of the tobacco or substitute therefor need be treated, and the thus-treated tobacco may be blended with other tobaccos before the ultimate tobacco product is formed. In such cases, the tobacco treated may have one or more 2,4,6-Trimethylcyclohexanemethanol and derivatives thereof of our invention in excess of the amounts or concentrations above indicated so that when blended with other tobaccos, the final product will have the percentage within the indicated range.

While our invention is particularly useful in the manufacture of smoking tobacco such as cigarette tobacco, cigar tobacco and pipe tobacco, other tobacco products formed from sheeted tobacco dust or fines may also be used. As stated supra, 2,4,6-Trimethylcyclohexanemethanol and derivatives thereof of our invention can be incorporated with materials such as filter tip materials, seam paste, packaging materials and the like which are used along with the tobacco to form a product adapted for smoking. Furthermore, 2,4,6-Trimethylcyclohexanemethanol and derivatives thereof of our invention can be added to certain tobacco substitutes of natural or synthetic origin (e.g., dried lettuce leaves) and, accordingly, by the term "tobacco" as used throughout this specification is meant any composition intended for human consumption, by smoking or otherwise, whether composed of tobacco plant parts or substitute materials or both.

It will thus be apparent that 2,4,6-Trimethylcyclohexanemethanol and derivatives thereof of our invention can be utilized to alter, modify, augment or enhance sensory properties, particularly organoleptic properties, such as flavor(s) and/or fragrance(s) of a wide variety of consumable materials.

The following examples serve to illustrate our invention, and this invention is to be considered restricted thereto only as indicated in the appended claims.

All parts and percentages given herein are by weight unless otherwise specified.

EXAMPLE I

Preparation of 2,4,6-Trimethylcyclohex-3-enylmethanol

Reaction:

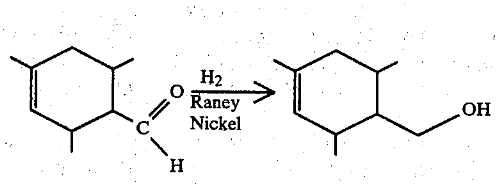

2,4,6-Trimethylcyclohex-3-enylcarboxaldehyde (500 grams, 3.25 moles) and 10 grams of Raney Nickel are charged to a one liter autoclave. The reaction mass is heated to 80° C. and the hydrogen pressure set at 500 psi (pounds per square inch). After 10 hours of hydrogenation, 3.5 moles of hydrogen are taken up and the reaction mass is cooled. The resulting oil is filtered, and the autoclave and filter cake are rinsed with isopropanol. Fractional distillation through a 1½"×12" Goodloe® packed column affords 463 grams (90% of theory) of 2,4,6-Trimethylcyclohex-3-enylmethanol (b.p. 82° C. at 5 mm).

Figure 1:
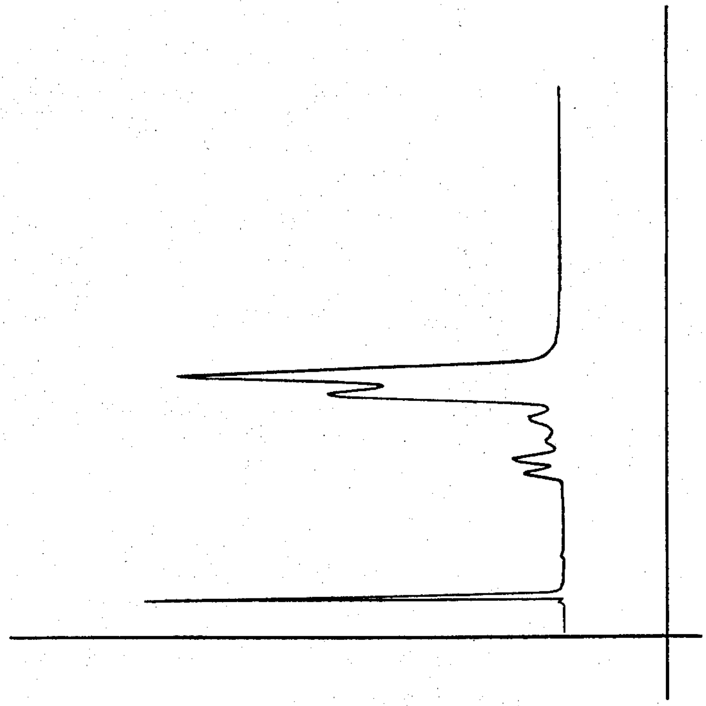
FIG. 1 is the GLC profile for the reaction product of Example I containing the compound having the structure.

FIG. 1 shows the GLC of the crude oil before distillation (¼"×10' 10% SE-30 packed column, 180° C. isothermal).

FIG. 2 shows the NMR spectrum of fraction 6 of the distillation.

FIG. 3 shows the IR spectrum of fraction 6 of the distillation.

EXAMPLE II

Preparation of 2,4,6-Trimethylcyclohex-3-enylmethylacetate

Reaction:

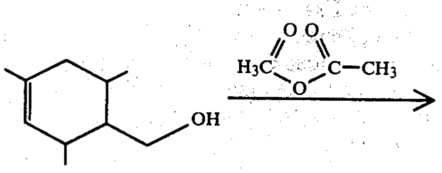

-continued

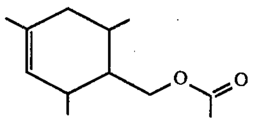

A solution of 291 grams (1.89 moles) of 2,4,6-Trimethylcyclohex-3-enylmethanol (from Example I) and 300 grams (2.94 moles) of acetic anhydride are heated with stirring at reflux (137° C.) for one hour. The reaction mass is cooled to 70° C., and 500 mls of water are added thereto with stirring. Two clear layers are formed. The bottom (aqueous) layer is discarded and the top layer is washed successively with water, 5% sodium carbonate solution, and water. The resulting oil is fractionally distilled through a 1½"×12" Goodloe® packed column to afford 325 grams (88% based on 2,4,6-Trimethylcyclohex-3-enylmethanol) of 2,4,6-Trimethylcyclohex-3-enylmethylacetate (b.p. 60° C. at 1.2 mm).

FIG. 4 is the GLC trace of the crude reaction product (1"×10" 10% SE-30 packed column, 180° C. isothermal).

FIG. 5 represents the NMR spectrum of fraction 8.

FIG. 6 represents the IR spectrum of fraction 8.

EXAMPLE III

Preparation of 2,4,6-Trimethylcyclohexanylmethanol

Reaction:

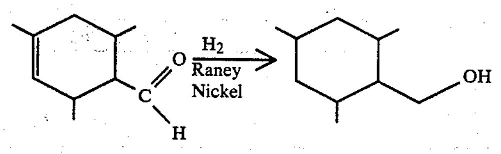

2,4,6-Trimethylcyclohex-3-enylcarboxaldehyde (500 grams, 3.25 moles) and 10 grams of Raney Nickel are charged to a one liter autoclave. The reaction mass is heated to 150° C. and the hydrogen pressure is set at 1000 psi (pounds per square inch). After 3½ hours, 6.3 moles of hydrogen are absorbed and the reaction mass is cooled. The resulting oil is filtered, and the autoclave and filter cake are washed with isopropanol. Fractional distillation through a 1½"×12" Goodloe® packed column affords 436 grams (85% of theory) of 2,4,6-Trimethylcyclohexanylmethanol (b.p. 76° C. at 5 mm).

FIG. 7 represents the GLC trace of the crude reaction product (¼"×10' 10% SE-30 packed column, 180° C. isothermal).

FIG. 8 represents the NMR spectrum of fraction 7 of the distillation.

FIG. 9 represents the IR spectrum of fraction 7 of the distillation.

EXAMPLE IV

Preparation of Trimethylcyclohexanylmethanolacetate

Reaction:

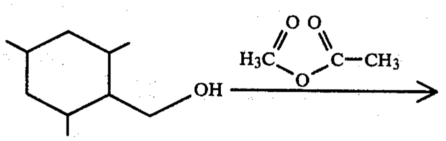

-continued

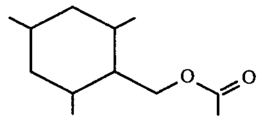

A solution of 323 grams (2.02 moles) of 2,4,6-Trimethylcyclohexanyl (from Example 3) and 300 grams (2.94 moles) of acetic anhydride are heated with stirring at reflux (137° C.) for one hour. The reaction mass is cooled to 70° C., and 500 mls of water are added thereto with stirring. Two clear layers are formed. The bottom (aqueous) layer is discarded and the top layer is washed successively with water, 5% sodium carbonate solution and water. The resulting oil is fractionally distilled through a 1½"×12" Goodloe® packed column to afford 362 grams (91% based on 2,4,6-Trimethylcyclohexanylmethanol) of 2,4,6-Trimethylcyclohexanylmethylacetate (b.p. 76° C. at 3 mm).

FIG. 10 shows the GLC trace of the crude reaction product (¼"×10", 10% SE-30 packed column, 180° C. isothermal).

FIG. 11 shows the NMR spectrum of fraction 6.

FIG. 12 shows the IR spectrum of fraction 6.

EXAMPLE V

Toothpaste Flavor Formulation

The following basic toothpaste flavor formulation is prepared:

| Ingredients | Parts by Weight |
|---|---|
| Cardamon Oil | 0.2 |
| Clove Oil | 1.0 |
| Spearmint Oil | 2.0 |
| Peppermint Oil | 96.8 |

This flavor formulation is divided into three portions. To the first portion, nothing is added. To the second portion, eight parts by weight of the first portion is combined with two parts by weight of anethol. Eight parts by weight of the second portion of this flavor is then combined with two parts by weight of 2,4,6-Trimethylcyclohexanemethanol prepared according to Example III.

Each of the three flavors are compared in water at the rate of 10 ppm and evaluated by a bench panel. Each of the three flavors has sweet anise-like characteristics, but the flavor containing the 2,4,6-Trimethylcyclohexanemethanol also has minty, herbaceous and spearmint-like nuances in addition to the licorice-related note and fennel notes. Therefore, the flavor containing the 2,4,6-Trimethylcyclohexanemethanol is preferred over the flavors not containing said 2,4,6-Trimethylcyclohexanemethanol and, in addition, the 2,4,6-Trimethylcyclohexanemethanol augments and enhances the anise-like flavor.

EXAMPLE VI

Perfume Composition

The following mixture is prepared:

| Ingredients | Parts by Weight |
|---|---|
| Phenylacetic acid | 70.0 |
| Coumarin | 20.0 |

-continued

| Ingredients | Parts by Weight |
|---|---|
| Phenylethylphenyl acetate | 100.0 |
| Phenyl ethyl alcohol | 5.0 |
| Benzyl benzoate | 100.0 |
| Dimethylphenylethyl carbinol | 10.0 |
| Methyl anthranilate | 5.0 |
| Beta ionone | 10.0 |
| In the alternative, 2,4,6-Trimethyl-3-cyclohexene-1-methanol produced according to Example I or 2,4,6-Trimethyl-3-cyclohexene-1-methanolacetate produced according to Example II, or 2,4,6-Trimethyl-cyclohexane-methanol produced according to Example III, or 2,4,6-Trimethyl-cyclohexanemethanol-acetate produced according to Example IV | 30.0 |

The 2,4,6-Trimethyl-3-cyclohexene-1-methanol produced according to Example I imparts the fresh green floral aroma with geranium undertone to this honey fragrance. The 2,4,6-Trimethyl-3-cyclohexene-1-methanol acetate produced according to Example II gives a fresh, fruity, floral, Freesia-type aroma with ionone-like nuances to this honey fragrance. The 2,4,6-Trimethylcyclohexanemethanol produced according to Example III gives a sweet spicy aroma with a minty rose background to this honey fragrance.

The 2,4,6-Trimethylcyclohexanemethanolacetate produced according to Example IV gives a spicy, fruity, methylionone-like character to this honey fragrance.

When the materials produced according to Examples I, II, III and IV are combined in equal portions at 7.5 parts by weight each the combined character given to the honey fragrance is a sweet spicy; fresh green, floral, fruity; Freesia-like; methylionone-like aroma with geranium and ionone-like topnotes and minty rose undertones. These aromas can be imparted by means of varying the proportions of each of the ingredients of this mixture containing the compounds of Examples I, II, III and IV within the following ranges:

(i) The 2,4,6-Trimethyl-3-cyclohexene-1-methanol produced according to Example I; from 20 up to 80%.

(ii) The 2,4,6-Trimethyl-3-cyclohexene-1-methanolacetate produced according to Example II; from 20 up to 80%.

(iii) The 2,4,6-Trimethylcyclohexanemethanol produced according to Example III; from 10 up to 30%.

(iv) The 2,4,6-Trimethylcyclohexanemethanolacetate produced according to Example IV; from 10 up to 30%.

EXAMPLE VII

Preparation of a Cosmetic Powder Composition

A cosmetic powder is prepared by mixing in a ball mill, 100 g of talcum powder with 0.25 g of one of the following materials:

(a) The perfume composition of Example VI.

(b) The 2,4,6-Trimethyl-3-cyclohexene-1-methanol prepared according to Example I.

(c) The 2,4,6-Trimethyl-cyclo-3-cyclohexene-1-methanolacetate produced according to Example II.

(d) The 2,4,6-Trimethyl-cyclohexanemethanol produced according to Example III.

(e) The 2,4,6-Trimethyl-cyclohexanemethanolacetate produced according to Example IV.

Composition (a) imparts a honey fragrance with the notes as described in Example VI to this cosmetic powder. Composition (b) imparts the fresh green, floral aroma with a geranium character to this composition. Composition (c) imparts a fresh, fruity, floral, Freesia-like aroma with ionone nuances to this composition. Composition (d) imparts a sweet spicy, green aroma with a minty rose background to this composition. Composition (e) imparts a methylionone-like, spicy, fruity aroma to this composition.

EXAMPLE VIII

Perfumed Liquid Detergents

Concentrated liquid detergents (Lysine salt of n-dodecylbenzene sulfonic acid as more specifically described in U.S. Pat. No. 3,948,818 issued on Apr. 6, 1976) with the aroma nuances listed below are prepared containing 0.10%, 0.15%, 0.20%, 0.25%, 0.30%, 0.50% and 1% of the materials set forth below. They are prepared by adding and homogeneously mixing the appropriate quantity of said materials listed below in the liquid detergents. The detergents all possess aromas as set forth below:

(a) The perfume composition of Example VI.

(b) The 2,4,6-Trimethyl-3-cyclohexene-1-methanol prepared according to Example I.

(c) The 2,4,6-Trimethyl-cyclo-3-cyclohexene-1-methanolacetate produced according to Example II.

(d) The 2,4,6-Trimethyl-cyclohexanemethanol produced according to Example III.

(e) The 2,4,6-Trimethyl-cyclohexanemethanolacetate produced according to Example IV.

Composition (a) imparts a honey fragrance with the notes as described in Example VI to this cosmetic powder. Composition (b) imparts the fresh green, floral aroma with a geranium character to this composition. Composition (c) imparts a fresh, fruity, floral, Freesia-like aroma with ionone nuances to this composition. Composition (d) imparts a sweet spicy, green aroma with a minty rose background to this composition. Composition (e) imparts a methylionone-like, spicy, fruity aroma to this composition.

EXAMPLE IX

Preparation of Cologne and Handkerchief Perfumes

The compositions as set forth below are incorporated into colognes at concentrations of 2.0%, 2.5%, 3.0%, 3.5%, 4.0%, 4.5%, and 5.0% in 85%, 90% and 95% food grade ethanol; and into handkerchief perfumes at concentrations of 10%, 15%, 20%, 25%, 30%, 35% and 50% (in 80%, 85%, 90% and 95% food grade ethanol). The following aromas are imparted to the colognes and to the handkerchief perfumes at all levels indicated above:

(a) The perfume composition of Example VI.

(b) The 2,4,6-Trimethyl-3-cyclohexene-1-methanol prepared according to Example I.

(c) The 2,4,6-Trimethyl-cyclo-3-cyclohexene-1-methanolacetate produced according to Example II.

(d) The 2,4,6-Trimethyl-cyclohexanemethanol produced according to Example III.

(e) The 2,4,6-Trimethyl-cyclohexanemethanolacetate produced according to Example IV.

Composition (a) imparts a honey fragrance with the notes as described in Example VI to this cosmetic powder. Composition (b) imparts the fresh green, floral aroma with a geranium character to this composition. Composition (c) imparts a fresh, fruity, floral, Freesia-like aroma with ionone nuances to this composition. Composition (d) imparts a sweet spicy, green aroma with a minty rose background to this composition. Composition (e) imparts a methylionone-like, spicy, fruity aroma to this composition.

EXAMPLE X

Utilizing the procedure of Example I of column 15 of U.S. Pat. No. 3,632,396, a nonwoven cloth substrate useful as a dryer-added fabric-softening article of manufacture is prepared wherein the substrate, the substrate coating and the outer coating and the perfuming material are as follows:

1. a water "dissolvable" paper ("Dissolvo Paper");
2. Adogen 448 (m.p. about 140° F.) as the substrate coating; and
3. an outer coating having the following formulation (m.p. about 150° F.):

57 percent $C_{20-22}$ HAPS 22 percent isopropyl alcohol 20 percent antistatic agent 1 percent of the material set forth in Table II below and giving rise to the aroma nuances as set forth in Table II.

TABLE II

| NAME OF COMPOUND | FRAGRANCE CHARACTERISTICS |
|---|---|
| Perfumed composition of Example VI. | Honey fragrance. |
| 2,4,6-Trimethyl-3-cyclohexene-1-methanol prepared according to Example I. | Fresh green, floral aroma with a geranium character. |
| 2,4,6-Trimethyl-cyclo-3-cyclohexene-1-methanolacetate produced according to Example II. | Fresh, fruity, floral, Freesia-like aroma with ionone nuances. |
| 2,4,6-Trimethyl-cyclohexanemethanol produced according to Example III. | Sweet, spicy, green aroma with a minty rose background. |
| 2,4,6-Trimethyl-cyclohexanemethanolacetate produced according to Example IV. | Methylionone-like, spicy, fruity aroma. |

Fabric-softening compositions prepared as set forth above having the above aroma characteristics essentially consist of a substrate having a weight of about 3 grams per 100 square inches, a substrate coating of about 1.85 grams per 100 square inches of substrate and an outer coating of about 1.4 grams per 100 square inches of substrate, thereby providing a total aromatized substrate and outer coating weight ratio of about 1:1 by weight of the substrate. The aromas as set forth in Table II above are imparted in a pleasant manner to the head space in the dryer on operation thereof using the said dryer added fabric softening nonwoven fabric.

EXAMPLE XI

A liquid detergent composition is prepared according to Example IV of United Kingdom Pat. No. 1,498,520 whereby the following ingredients are admixed:

| Ingredient | Weight % |
|---|---|
| Coconut alcohol ethoxylate | 30% |
| Linear alkyl benzene sulfonate, triethanolamine salt (alkyl = $C_{11.8}$ avg.) | 10% |
| Potassium chloride | 3% |
| Triethanolamine | 3% |

-continued

| Ingredient | Weight % |
|---|---|
| Triethanolammonium citrate | 2% |
| Ethyl alcohol | 5% |
| Soil release ether "D" | 1.0% |
| Composition as set forth in Table III | 3.0% |

The soil release ether "D" is defined according to Table II on page 15 of United Kingdom Pat. No. 1,498,520.

This composition is prepared by admixing all of the ingredients exclusive of soil release ether "D" and agitating the mixture until all electrolytes are dissolved. Soil release ether "D" is then admixed with the solution in the form of a dry powder which passes through a 150 mesh standard sieve. The resulting composition is in the liquid state and is easily pourable. The composition is found not to redden on contact with plastic bottles, does not gel when diluted with water and has a long-lasting aroma composition as defined in the following Table III when the following 2,4,6-Trimethylcyclohexanemethanol or derivatives thereof of our invention are added thereto:

TABLE III

| NAME OF COMPOUND | FRAGRANCE CHARACTERISTICS |
|---|---|
| Perfume composition of Example VI. | Honey fragrance. |
| 2,4,6-Trimethyl-3-cyclohexene-1-methanol prepared according to Example I. | Fresh green, floral aroma with a geranium character. |
| 2,4,6-Trimethyl-cyclo-3-cyclohexene-1-methanolacetate produced according to Example II. | Fresh, fruity, floral, Freesia-like aroma with ionone nuances. |
| 2,4,6-Trimethyl-cyclohexanemethanol produced according to Example III. | Sweet, spicy, green aroma with a minty rose background. |
| 2,4,6-Trimethyl-cyclohexanemethanolacetate produced according to Example IV. | Methylionone-like, spicy, fruity aroma. |

This composition is added to an aqueous laundrying bath at a concentration of 0.20% (weight) at a temperature of 55° C., water hardness 7 grains/gallon and a pH of 10.0. Polyester and mixed polyester/cotton fabrics are laundered in the bath for a period of 10 minutes after which the fabrics are thoroughly rinsed with fresh water and dried at ambient temperatures. The fabrics are provided with a soil release finish. The head space above the fabrics has a pleasant faint aroma as indicated in Table III above.

EXAMPLE XII

Preparation of Soap Composition

One hundred grams of soap chips (obtained by chopping up four bars of IVORY ® (Trademark product of the Proctor and Gamble Company of Cincinnati, Ohio) are intimately admixed with one gram each of the formulations as set forth below until homogeneous compositions are obtained. In each of the cases, the homogeneous compositions are heated under eight atomspheres pressure at 180° C. for a period of three hours and the resulting liquids are placed into soap molds. The resulting soap cakes, on cooling, manifest the following aromas using the following compositions:

(a) The perfume composition of Example VI.

(b) The 2,4,6-Trimethyl-3-cyclohexene-1-methanol prepared according to Example I.

(c) The 2,4,6-Trimethyl-cyclo-3-cyclohexene-1-methanolacetate produced according to Example II.

(d) The 2,4,6-Trimethyl-cyclohexanemethanol produced according to Example III.

(e) The 2,4,6-Trimethyl-cyclohexanemethanolacetate produced according to Example IV.

Composition (a) imparts a honey fragrance with the notes as described in Example VI to this cosmetic powder. Composition (b) imparts the fresh green, floral aroma with a geranium character to this composition. Composition (c) imparts a fresh, fruity, floral, Freesia-like aroma with ionone nuances to this composition. Composition (d) imparts a sweet spicy, green aroma with a minty rose background to this composition. Composition (e) imparts a methylionone-like, spicy, fruity aroma to this composition.

EXAMPLE XIII

Preparation of a Solid Detergent Composition

A detergent is prepared from the following ingredients according to Example I of Canadian Pat. No. 1,007,948:

| | Percent by Weight |
|---|---|
| "Neodol 45-11" (a $C_{14}$-$C_{15}$ alcohol ethoxylated with 11 moles of ethylene oxide) | 12 |
| Sodium carbonate | 55 |
| Sodium citrate | 20 |
| Sodium sulfate, water brighteners | q.s. |

This detergent is a "phosphate-free" detergent. A total of 100 grams of this detergent is admixed with 0.15 grams of each of the materials as set forth below. Each of the detergent samples has an excellent aroma as described below:

(a) The perfume composition of Example VI.

(b) The 2,4,6-Trimethyl-3-cyclohexene-1-methanol prepared according to Example I.

(c) The 2,4,6-Trimethyl-cyclo-3-cyclohexene-1-methanolacetate produced according to Example II.

(d) The 2,4,6-Trimethyl-cyclohexanemethanol produced according to Example III.

(e) The 2,4,6-Trimethyl-cyclohexanemethanolacetate produced according to Example IV.

Composition (a) imparts a honey fragrance with the notes as described in Example VI to this cosmetic powder. Composition (b) imparts the fresh green, floral aroma with a geranium character to this composition. Composition (c) imparts a fresh, fruity, floral, Freesia-like aroma with ionone nuances to this composition. Composition (d) imparts a sweet spicy, green aroma with a minty rose background to this composition. Composition (e) imparts a methylionone-like, spicy, fruity aroma to this composition.

EXAMPLE XIV

A tobacco blend is made up by mixing the following materials:

| Ingredient | Parts by Weight |
|---|---|
| Bright | 40.1 |
| Burley | 24.9 |
| Maryland | 1.1 |

-continued

| Ingredient | Parts by Weight |
|---|---|
| Turkish | 11.6 |
| Stem (flue cured) | 14.2 |
| Glycerine | 2.8 |
| Water | 5.3 |

The above tobacco is used in producing cigarettes, and the following formulation is compounded and incorporated into each of these cigarettes:

| Ingredient | Parts by Weight |
|---|---|
| Ethyl butyrate | .05 |
| Ethyl valerate | .05 |
| Maltol | 2.00 |
| Cocoa extract | 26.00 |
| Coffee extract | 10.00 |
| Ethyl alcohol | 20.00 |
| Water | 41.90 |

The above flavor is incorporated into model "filter" cigarettes at the rate of 0.1%. One-third of these model cigarettes are treated in the tobacco section with either 2,4,6-Trimethyl-3-cyclohexene-1-methanolacetate produced according to Example II or 2,4,6-Trimethyl-3-cyclohexene-1-methanol produced according to Example I at 100, 200 and 300 ppm per cigarette. Another one-third of these model cigarettes are treated in the filter with either 2,4,6-Trimethyl-3-cyclohexene-1-methanolacetate produced according to Example II or 2,4,6-Trimethyl-3-cyclohexene-1-methanol produced according to Example I at the rate of $2\times10^{-5}$ gm. When evaluated by paired comprison, the cigarettes treated both in the tobacco and in the filter with the 2,4,6-Trimethyl-3-cyclohexene-1-methanol and 2,4,6-Trimethyl-3-cyclohexene-1-methanolacetate are found, in smoke flavor, to have sweet, floral, green and herbaceous aroma nuances causing the tobacco to be more natural-like. In general, an excellent hay tobacco aroma and taste is imparted prior to and on smoking in both the main stream and in the side stream by the products of Examples I, as well as II.

EXAMPLE XV

Mint Flavor Formulation

The following mint flavor is prepared:

| Ingredients | Parts by Weight |
|---|---|
| Peppermint Oil | 60.0 |
| Spearmint Oil | 38.0 |
| 2,4,6-Trimethylcyclohexanemethanol prepared according to Example III | 2.0 |

The 2,4,6-Trimethylcyclohexanemethanol prepared according to Example III imparts a minty, herbaceous, fruity, floral and fresh aroma and flavor characteristic of great intensity to this mint flavor formulation.

EXAMPLE XVI

A. Powder Flavor Formulation

20 Grams of the flavor composition of Example XV is emulsified in a solution containing 300 gm gum acacia and 700 gm water. The emulsion is spray-dried with a Bowen Lab Model Drier utilizing 260 c.f.m. of air with an inlet temperature of 500° F., an outlet temperature of 200° F. and a wheel speed of 50,000 rpm.

B. Sustained Release Flavor

The following mixture is prepared:

| Ingredients | Parts by Weight |
|---|---|
| Liquid mint Flavor | |
| Composition of Example XIII | 20 |
| Propylene glycol | 9 |
| Cab-O-Sil ® M-5 | 5.00 |
| (Brand of Silica produced by the Cabot Corporation of 125 High Street, Boston, Mass. 02110; | |
| Physical Properties: | |
| Surface Area: 200 $m^2gm$ | |
| Nominal particle size: 0.012 microns | |
| Density: 2.3 lbs/cu.ft.) | |

The Cab-O-Sil is dispersed in the liquid mint flavor compositions of Example XV with vigorous stirring, thereby resulting in a viscous liquid. 71 Parts by weight of the powder flavor composition of Part A, supra, is then blended into the said viscous liquid, with stirring, at 25° C. for a period of 30 minutes resulting in a dry, free flowing sustained release flavor powder.

EXAMPLE XVII

10 Parts by weight of 50 Bloom pigskin gelatin is added to 90 parts by weight of water at a temperature of 150° F. The mixture is agitated until the gelatin is completely dissolved and the solution is cooled to 120° F. 20 Parts by weight of the liquid flavor composition of Example XV is added to the solution which is then homogenized to form an emulsion having particle size typically in the range of 2–5 microns. This material is kept at 120° F. under which conditions the gelatin will not jell.

Coacervation is induced by adding slowly and uniformly 40 parts by weight of a 20% aqueous solution of sodium sulphate. During coacervation the gelatin molecules are deposited uniformly about each oil droplet as a nucleus.

Gelation is effected by pouring the heated coacervate mixture into 1,000 parts by weight of 7% aqueous solution of sodium sulphate at 65° F. The resulting jelled coacervate may be filtered and washed with water at temperatures below the melting point of gelatin, to remove the salt.

Hardening of the filtered cake, in this example, is effected by washing with 200 parts by weight of 37% solution of formaldehyde in water. The cake is then washed to remove residual formaldehyde.

EXAMPLE XVIII

Chewing Gum

100 Parts by weight of chicle are mixed with 4 parts by weight of the flavor prepared in accordance with Example XV. 300 Parts of sucrose and 100 parts of corn syrup are added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting mint flavors.

EXAMPLE XIX

Chewing Gum

100 Parts by weight of chicle are mixed with 18 parts by weight of the flavor prepared in accordance with Example XV. 300 Parts of sucrose and 100 parts of corn syrup are then added. Mixing is effected in a ribbon blender with jacketed side walls of the type manufactured by the Baker Perkins Co.

The resultant chewing gum blend is then manufactured into strips 1 inch in width and 0.1 inches in thickness. The strips are cut into lengths of 3 inches each. On chewing, the chewing gum has a pleasant, long lasting mint flavor.

EXAMPLE XX

Toothpaste Formulation

The following separate groups of ingredients are prepared:

| Parts by Weight | Ingredient |
|---|---|
| Group "A" | |
| 30.200 | Glycerine |
| 15.325 | Distilled Water |
| .100 | Sodium Benzoate |
| .125 | Saccharin Sodium |
| .400 | Stannous Fluoride |
| Group "B" | |
| 12.500 | Calcium Carbonate |
| 37.200 | Dicalcium Phosphate (Dihydrate) |
| Group "C" | |
| 2.000 | Sodium N-Lauroyl Sarcosinate (foaming agent) |
| Group "D" | |
| 1.200 | Flavor Material of Example XV |
| 100.00 - TOTAL | |

PROCEDURE:

1. The ingredients in Group "A" are stirred and heated in a steam jacketed kettle to 160° F.
2. Stirring is continued for an additional three to five minutes to form a homogeneous gel
3. The powders of Group "B" are added to the gel, while mixing, until a homogeneous paste is formed
4. With stirring, the flavor of "D" is added and lastly the sodium-n-lauroyl sarcosinate
5. The resultant slurry is then blended for one hour. The completed paste is then transferred to a three roller mill and then homogenized, and finally tubed.

The resulting toothpaste when used in a normal toothbrushing procedure yields a pleasant mild flavor, of constant strong intensity throughout said procedure (1-1.5 minutes).

EXAMPLE XXI

Chewable Vitamin Tablets

The flavor material produced according to the process of Example XV is added to a Chewable Vitamin Tablet. Formulation at a rate of 10 gm/Kg which Chewable Vitamin Tablet formulation is prepared as follows:

In a Hobart Mixer, the following materials are blended to homogeneity:

| | Gms/1000 Tablets |
|---|---|
| Vitamin C (ascorbic acid) as ascorbic acid-sodium ascorbate mixture 1:1 | 70.11 |
| Vitamin $B_1$ (thiamine mononitrate) as Rocoat ® thiamine mononitrate 33⅓% (Hoffman La Roche) | 4.0 |
| Vitamin $B_2$ (riboflavin) as Rocoat ® riboflavin 33⅓% | 5.0 |
| Vitamin $B_6$ (pyridoxine hydrochloride) as Rocoat ® pyridoxine hydrochloride 33⅓% | 4.0 |
| Niacinamide as Rocoat ® niacinamide 33⅓% | 33.0 |
| Calcium pantothenate | 11.5 |
| Vitamin $B_{12}$ (cyanocobalamin) as Merck 0.1% in gelatin | 3.5 |
| Vitamin E (dl-alpha tocopheryl acetate) as dry Vitamin E acetate 33⅓% | 6.6 |
| d-Biotin | 0.044 |
| Flavor of Example XV | (as indicated above) |
| Certified lake color | 5.0 |
| Sweetener - sodium saccharin | 1.0 |
| Magnesium stearate lubricant | 10.0 |
| Mannitol q.s. to make | 500.0 |

Preliminary tablets are prepared by slugging with flat-faced punches and grinding the slugs to 14 mesh. 13.5 gm dry Vitamin A Acetate and 0.6 gm Vitamin D are then added as beadlets. The entire blend is then compressed using concave punches at 0.5 gm each.

Chewing of the resultant tablets yields a pleasant, long-lasting mint flavor for a period of 15 minutes.

EXAMPLE XXII

Chewing Tobacco

Onto 100 pounds of tobacco for chewing (85% Wisconsin leaf and 15% Pennsylvania leaf) the following casing is sprayed at a rate of 30%:

| Ingredients | Parts by Weight |
|---|---|
| Corn Syrup | 60 |
| Licorice | 10 |
| Glycerine | 20 |
| Fig Juice | 4.6 |
| Prune Juice | 5 |
| Mint flavor of Example XV | 0.04 |

The resultant product is redried to a moisture content of 20%. On chewing, this tobacco has an excellent cooling mint flavor nuance in conjunction with the tobacco notes.

What is claimed is:

1. A process for augmenting or enhancing the spicy aroma of a perfume composition or cologne comprising the step of intimately admixing with a perfume base or a cologne base from 0.5% up to 50% by weight of said perfume composition or said cologne of 2,4,6-trimethyl-3-cyclohexene-1-methanol having the structure:

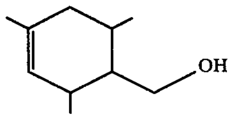

* * * * *